US009492124B2

(12) United States Patent
Qian et al.

(10) Patent No.: US 9,492,124 B2
(45) Date of Patent: Nov. 15, 2016

(54) SYSTEM AND METHOD FOR TREATMENT PLANNING OF ORGAN DISEASE AT THE FUNCTIONAL AND ANATOMICAL LEVELS (75) Inventors: Jian-Zhong Qian, Princeton Junction, NJ (US); Xiaolan Zeng, Princeton, NJ (US); Guo-Qing Wei, Plainsboro, NJ (US); Li Fan, Belle Mead, NJ (US)

(73) Assignees: EDDA TECHNOLOGY, INC., Princeton, NJ (US); EDDA TECHNOLOGY MEDICAL SOLUTIONS (SUZHOU) LTD., Suzhou (CN)

( * ) Notice: Subject to any disclaimer, the term of this patent is extended or adjusted under 35 U.S.C. 154(b) by 0 days.

(21) Appl. No.: 13/343,795

(22) Filed: Jan. 5, 2012

(65) Prior Publication Data

US 2012/0209108 A1 Aug. 16, 2012

Related U.S. Application Data

(60) Provisional application No. 61/430,458, filed on Jan. 6, 2011.

(51) Int. Cl.
*A61B 6/03* (2006.01)
*A61B 6/00* (2006.01)
*A61N 5/10* (2006.01)
*G06T 7/00* (2006.01)
*G06F 19/00* (2011.01)

(52) U.S. Cl.
CPC ............... *A61B 6/037* (2013.01); *A61B 6/032* (2013.01); *A61B 6/5235* (2013.01); *A61N 5/1039* (2013.01); *G06T 7/0083* (2013.01); *G06F 19/321* (2013.01); *G06F 19/3481* (2013.01); *G06T 2207/10081* (2013.01); *G06T 2207/10108* (2013.01); *G06T 2207/20221* (2013.01); *G06T 2207/30056* (2013.01)

(58) Field of Classification Search
CPC ..... A61B 6/5235; A61B 6/5229; G06T 7/0083; G06T 2207/10081; G06T 2207/10108; G06T 2207/20221
See application file for complete search history.

(56) References Cited

U.S. PATENT DOCUMENTS 7,336,809 B2   2/2008   Zeng et al.
8,260,013 B2   9/2012   Pekar
(Continued)

FOREIGN PATENT DOCUMENTS

CN   101401725 A   4/2009
CN   101061520 A   10/2010
(Continued)

OTHER PUBLICATIONS

Rueckert, Nonrigid Registration Using Free-Form Deformations: Application to Breast MR Images, IEEE Transactions on Medical Imaging, vol. 18, No. 8, Aug. 1999.*
(Continued)

*Primary Examiner* — Serkan Akar
(74) *Attorney, Agent, or Firm* — Pillsbury Winthrop Shaw Pittman LLP (57) ABSTRACT

The present disclosure relates to a system and method for planning treatment of soft organs utilizing CT and SPECT image technology. The systems and method combine the segmented CT images with the SPECT image to form a combined image and treatment plan utilizing the images of both systems.

22 Claims, 6 Drawing Sheets

(56) References Cited

U.S. PATENT DOCUMENTS

| | | |
|---|---|---|
| 2003/0099385 A1 | 5/2003 | Zeng |
| 2006/0030769 A1* | 2/2006 | Ramamurthy et al. ....... 600/407 |
| 2006/0258933 A1 | 11/2006 | Ellis et al. |
| 2008/0050000 A1 | 2/2008 | Blaffert et al. |
| 2008/0292194 A1 | 11/2008 | Schmidt et al. |
| 2010/0316268 A1 | 12/2010 | Liang et al. |
| 2010/0316277 A1 | 12/2010 | Fan et al. |
| 2011/0054295 A1* | 3/2011 | Masumoto et al. .......... 600/407 |

FOREIGN PATENT DOCUMENTS

| | | | |
|---|---|---|---|
| NL | WO2009/109905 | * 11/2009 | |
| WO | WO 2011/010231 | * 1/2011 | ............... G06T 7/00 |

OTHER PUBLICATIONS

International Search Report corresponding to PCT/US12/20259 dated Apr. 25, 2012.
Office Action issued on Dec. 1, 2014 in Chinese Application No. 201280004701.1.
Office Action issued on Apr. 5, 2016 in Chinese Application No. 201280004701.1.
Office Action issued on Aug. 11, 2016 in Chinese Application No. 201280004701.1.

* cited by examiner

SYSTEM AND METHOD FOR TREATMENT PLANNING OF ORGAN DISEASE AT THE FUNCTIONAL AND ANATOMICAL LEVELS

CROSS REFERENCE TO RELATED APPLICATIONS

This application claims priority from U.S. Provisional Application No. 61/430,458 filed Jan. 6, 2011 the disclosure of which is incorporated herein by reference in its entirety.

TECHNICAL FIELD

The present teaching relates to system and methods for treatment planning of soft organ disease in medical imaging. More specifically, the present teaching relates to methods and systems for treatment planning combining functional and anatomical information in SPECT and CT images.

BACKGROUND

Computerized Tomography or CT modality has been widely used for diagnosis and treatment follow-up purposes. It can provide very detailed anatomical structures of the human organs. For example, in oncology, CT is used to monitor therapeutic responses of a treatment to tumors by measuring size changes. However, it takes a long time, e.g., several weeks, for a treatment to be reflected in the size change of a tumor. SPECT (single photon emission computed tomography) is a modality that can provide immediate metabolic measurement of a human organ and/or tumors, allowing one to discriminate healthy tissue from diseased tissue at the functional level. While both CT and SPECT provide imaging information, the imaging obtained from SPECT cannot provide sufficiently detailed anatomical structural information about the human organs in the same manner that CT does. Furthermore, SPECT image resolution is much lower than CT, so accurate treatment planning may not be possible in SPECT images alone. Recently CT and SPECT have been combined into one imaging device, allowing both CT and SPECT images to be referenced across each other. Currently, the utilization of SPECT-CT imaging is utilized mostly at the image level. For example, SPECT and CT images may be overlaid on each other for cross-referencing. In percutaneous treatment of liver lesions for example, such as by Radio-Frequency Ablation (RFA) or chemoembolization, it is desirable to plan the treatment based on both the anatomical information and functional information. Furthermore, functional and anatomical images may be combined together for a more accurate segmentation of liver lesions.

It is therefore highly desirable to combine the anatomical information from CT for regional analysis with the functional analysis aspect of SPECT for a treatment planning and treatment monitoring at both the anatomical and functional levels.

SUMMARY

In an embodiment of the present disclosure a system for treatment planning of a soft organ is disclosed. The system includes a first device for generating a functional image of a soft organ, a second device for generating a structural image of the soft organ, a segmentation unit for segmenting the structural image of the soft organ, a geometry transformation unit, a functional segmentation unit, a fusion unit for combining the functional segmentation of the soft organ with the structural segmentation of the soft organ, and a treatment planning unit.

In another embodiment, the soft organ is a liver. In a further embodiment the first device is a Single Photon Emission Computed Tomography device. In another embodiment, the second device is a Computerized Axial Tomography (CT) device. In another embodiment the structural imaging system further comprises an organ vascular segmentation unit. In another embodiment the system further comprising a first device-second device lesion segmentation unit. In still another embodiment the organ vascular segmentation unit generates a vascular image wherein the vascular image is combined with a functional image from the first device.

In still another embodiment a method implemented on a machine having at least one processor, storage, and a communication platform connected to a network for planning a treatment plan for a soft organ is disclosed. The method includes segmenting a soft organ image obtained from an imaging device in a first image space, mapping the segmented image into a second image space, defining a soft organ boundary in the second image space, segmenting defective organ regions within the soft organ boundary in the second image space, mapping the segmented defective regions identified in the second image space into the soft organ image obtained in the first image space, segmenting out target objects based on mapped defective regions and anatomical information in the first image space, segmenting out other structures based on the soft organ image in the first image space, combining the segmented images in the first image space and the second image space into a combined image, and generating a treatment plan based on the combined image.

In another embodiment, the soft organ is a liver. In another embodiment the target objects are tumors. In still another embodiment, the first image space is a CT image. In still another embodiment the second image space is a SPECT image. in still another embodiment, the defining of the liver boundary in the second image space is based on the image obtained in the first image space. In another embodiment, the segmenting of defective organ regions is based on a threshold measurement. In another embodiment segmenting the target object is based on an optimization that maximizes the combined gradient of images from the first image space and mapped images from the second image space and minimizes the intensity variance within the target object. In another embodiment the other structures are vascular structures. in another embodiment the target object is a tumor. In another embodiment the combined images from the first image space and mapped images from the second image space are CT and mapped SPECT images.

In still another embodiment a machine-readable tangible and non-transitory medium, having information for forming a treatment plan of soft organ disease, recorded thereon is disclosed. Wherein the information, when read by the machine, causes the machine to segment a soft organ image obtained from an imaging device in a first image space, map the segmented image into a second image space, define a soft organ boundary in the second image space, segment defective organ regions within the soft organ boundary in the second image space, map the segmented defective regions identified in the second image space into the soft organ image obtained in the first image space, segment out target objects based on mapped defective regions and anatomical information in the first image space, segment out other structures based on the soft organ image in the first image space, combine the segmented images in the first image space and the second image space into a combined image, and generate a treatment plan based on the combined image. In another embodiment of the medium, the soft organ is a liver. In still another embodiment of the medium, the target object is a tumor.

BRIEF DESCRIPTION OF THE DRAWINGS

The inventions claimed and/or described herein are further described in terms of embodiments. These embodiments are described in detail with reference to the drawings. These embodiments are non-limiting exemplary embodiments, in which like reference numerals represent similar structures throughout the several views of the drawings, and wherein:

DETAILED DESCRIPTION

The present teaching herein discloses a system and methods for treatment planning and follow-up of soft organ treatment using both functional and anatomical information. The disclosure herein references a system and method for the treatment planning and follow-up of liver lesions using both functional and anatomical information. The disclosed embodiments make reference to the liver as the soft organ under investigation. However, it is to be understood, treatment planning, follow-up, surgery and other procedures on any organs such as heart, lungs, kidneys, stomach, intestines, brain, or other soft organs may utilize and benefit from the present disclosure. Accordingly, for ease of clarity, reference to the liver is used to describe an embodiment of the system and method of the present disclosure, but, this is not to be a limitation, as will be understood by those skilled in the art, and does not limit the scope of the invention in any manner. The examples illustrated are based on SPECT-CT images. Other functional modalities, such as PET (Positron Emission Tomography) may also be used in a similar way. Furthermore, other modalities that provide anatomical information, such as MR, may be used in the place of CT for the present teaching.

Figure 1:
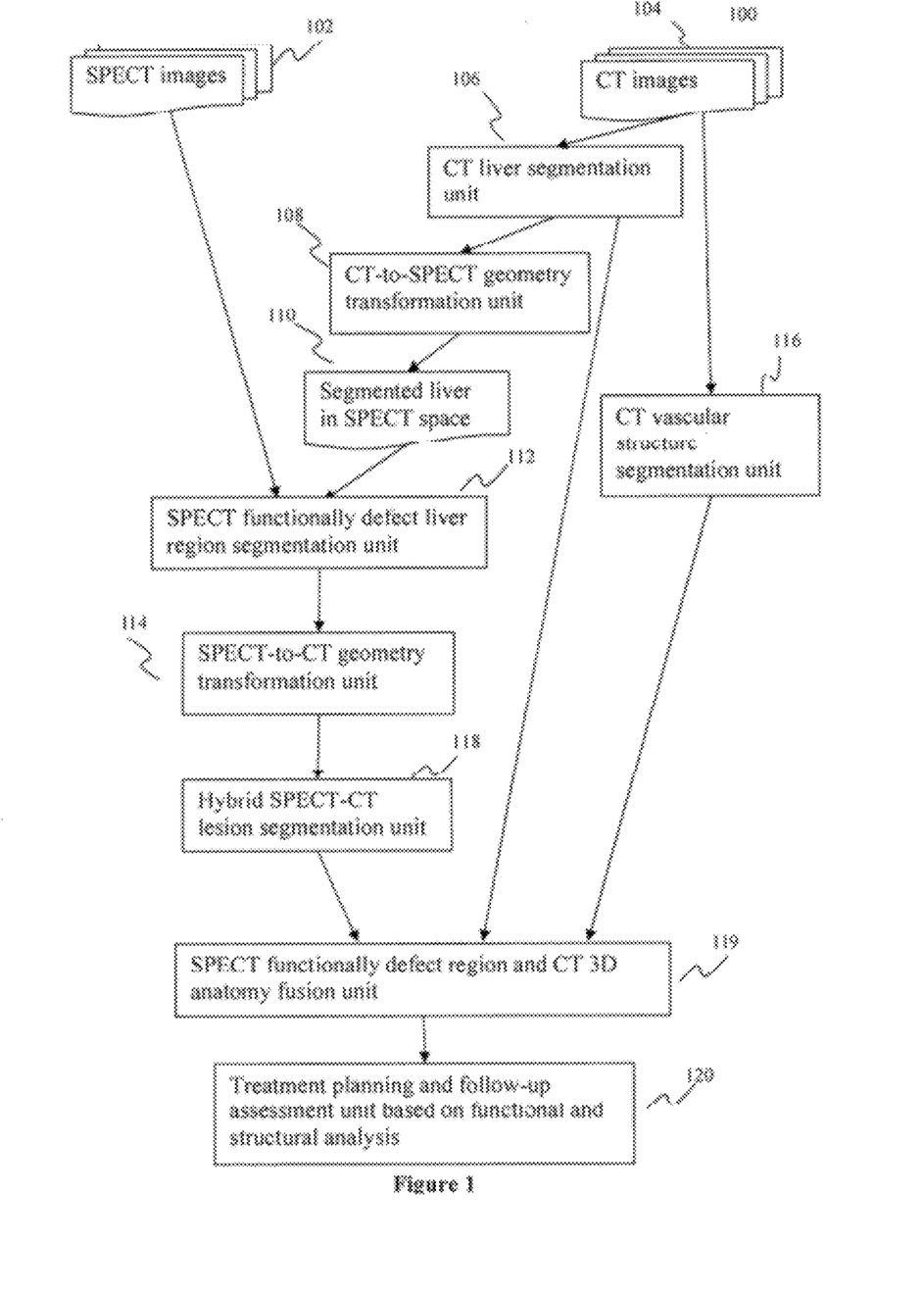
FIG. 1 depicts a system diagram for treatment planning and follow up assessment based on functional and anatomical images in accordance with the present disclosure.

FIG. 1 shows an exemplary system diagram of soft organ, treatment planning and monitoring system 100. The system may consist of a CT organ or liver segmentation unit 106, a CT-to-SPECT geometry transformation unit 108, SPECT functionally defect liver or soft organ region segmentation unit 112, a SPECT-to-CT geometry transformation unit 114, a hybrid SPECT-CT lesion segmentation unit 118, CT vascular structure segmentation unit 116, a SPECT-CT fusion unit 119, and a treatment planning and follow-up assessment unit 120. The CT segmented liver obtained by unit 106 is mapped by the unit 108 to the SPECT space based on the CT-SPECT geometrical transformation parameters. In the SPECT image space, the CT liver regions are used to confine the segmentation of the functionally defect liver region by unit 112. The functionally defect liver region in SPECT is combined with the CT images to derive a more accurate lesion segmentation in CT by unit 118. The segmented lesion, together with the functionally defect region from SPECT is fused, by unit 119, with other anatomical structures, such as vascular structures obtained by unit 116. The treatment planning and follow-up assessment unit 120 combines the functional analysis result in SPECT with the structural analysis result in CT to arrive at a treatment plan or an assessment of a treatment already performed.

Figure 2:
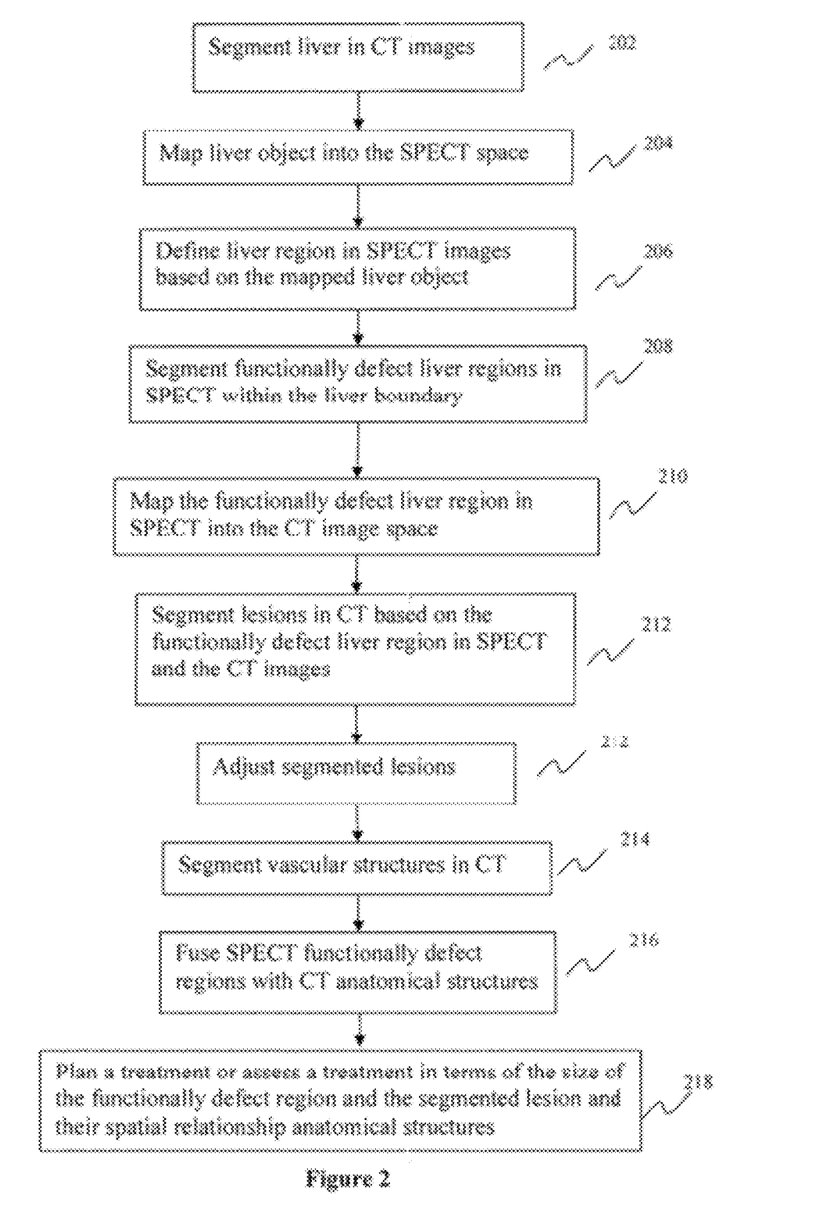
FIG. 2 depicts a flow diagram according to the present disclosure for treatment planning and follow up assessment based on functional and anatomical images.

FIG. 2 show an exemplary flow diagram of FIG. 1, according to one the present disclosure. First, a soft organ, such as a liver organ is segmented in CT at step 202, by any method known in the art, such as those disclosed in U.S. patent application Ser. No. 11/474,505 "Methods for interactive liver disease diagnosis" by Guo-Qing Wei et. al. The segmented liver may be mapped into the SPECT image space by step 204. The mapping may be based on either SPECT-CT mechanical registration parameters or based on known registration methods, such as D. Rueckert, L. Sonoda, C. Hayes, D. Hill, M. Leach, and D. Hawkes, "Nonrigid registration using free-form deformations: Application to breast MR images," IEEE Trans. Med. Imag., vol. 18, no. 8, pp. 712-721, August 1999, that can take into account breathing and body motion effect between the SPECT and CT images.

The mapped liver is used to define the liver boundary in SPECT images at step 206. Since functionally defect liver regions, such as lesions, do not show metabolic activity in SPECT, the intensity of such region is similar to the background, i.e., no illumination. Therefore, the CT liver boundary mapped to the SPECT space helps to define the liver boundary in SPECT. With the liver boundary defined in SPECT, functionally defective organ or liver regions may be segmented out within the organ or liver boundaries at step 208. The segmentation may be performed by thresholding or other advanced segmentation methods such as level set, e.g. Malladi, R., Sethian, J. A., and Vemuri, B. "Shape modeling with front propagation: A level set approach." IEEE Transactions on Pattern Analysis and Machine Intelligence 17, 2 (1995), 158-175. At step 210, the segmented functionally defective regions may be mapped to the CT image space based on the SPECT-CT geometric transformation parameters. At step 212, liver lesions may be segmented based on both the functional and anatomical information. The segmentation results may be interactively and manually adjusted by the operator. Adjustment may be any method of editing the image, such as a cut or a patch of the segmentation result or adjustment of segmentation parameters.

At step 214, vascular structures may be segmented out in CT using known methods. At step 216, the SPECT and CT information may be fused or combined into a unified image. In an embodiment of the present teaching, the fusion may be in the form of 3D object visualization, such as the display of both the functionally defective SPECT region, the segmented lesion, the segmented organ or liver and vascular structures in the same 3D space. It may be also in the form of overlay of functionally defective SPECT region and segmented lesion on the SPECT and CT images. At step 218, treatment planning or treatment assessment may be performed. In an embodiment, during treatment planning, based on the hybrid lesion segmentation result, a virtual cut may be performed based on the spatial relationship of the segmented lesion to the vascular structures. Additionally or alternatively, in percutaneous treatment of liver lesions, an ablation region may be defined based on the hybrid segmentation result. In one embodiment, a safety margin may be defined that specifies the distance of the virtual cut or ablation region to the surface of the hybrid segmented lesion. The function of the remaining liver may be computed based on the isotope count of the SPECT image for the remaining liver. In one embodiment, a user may adjust the safety margin size through a user interface. The function of the remnant liver as a result of the adjustment may be computed and displayed to the user. In another embodiment, different virtual cutting plans or ablation plans may be chosen by user and the remnant liver functions for the corresponding plans may be computed and displayed to user in different formats for decision making. In an embodiment, during treatment follow-up, the size of the segmented lesion from the hybrid segmentation may be compared with that of the same segmentation for SPECT-CT images of a prior time.

Figure 3A:
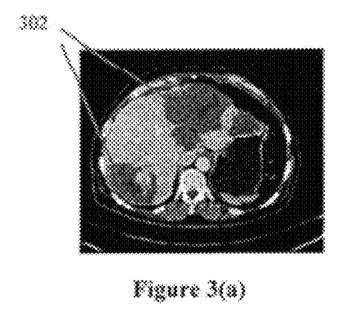
FIG. 3 is an example of a mapping of anatomical analysis result in CT to SPECT in accordance with the present disclosure.
Figure 3B:
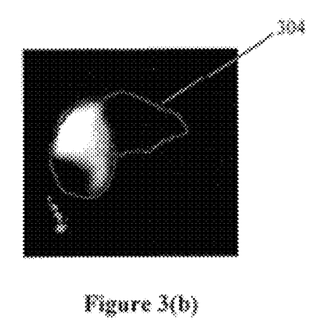
Figure 3C:
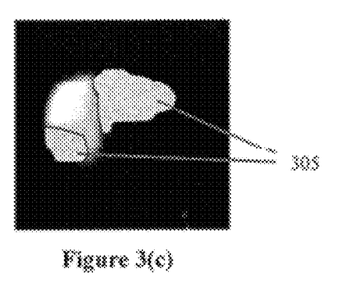

FIG. 3 depicts an example of an embodiment of the mapping between SPECT and CT image space for liver segments. FIG. 3(a) is one slice of a CT liver image sequence, where the areas 302 indicate diseased liver regions. FIG. 3(b) shows a slice of the SPECT image at the same location of the liver organ as the CT image, where 304 shows the liver boundary from CT images mapped onto the SPECT image space. As explained above, the dark regions, represent the diseased areas that show no uptake in SPECT. FIG. 3(c) shows the result of the segmentation of functionally defect regions 305 in SPECT based on the SPECT image intensity and liver boundary of FIG. 3(b).

Figure 4:
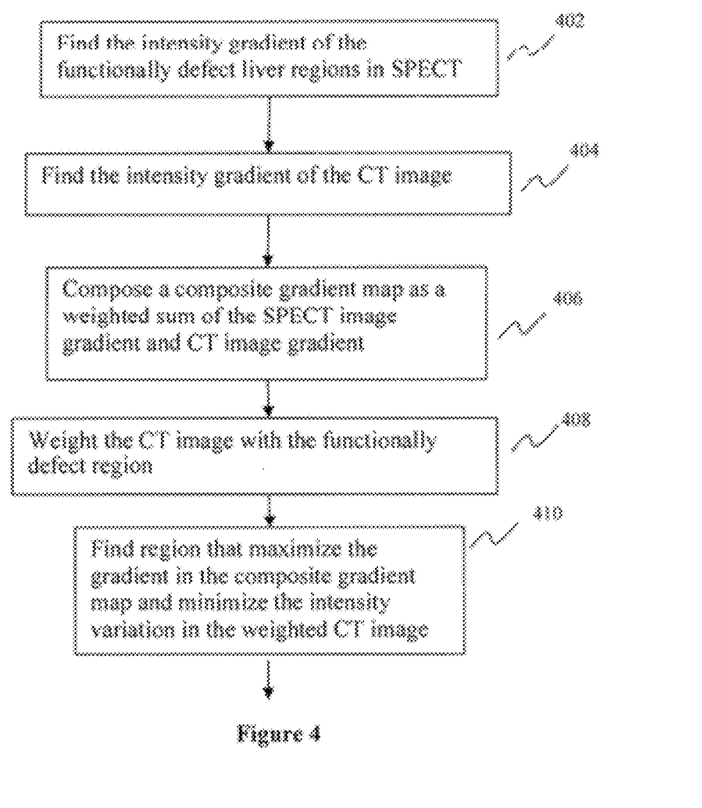
FIG. 4 depicts a flow diagram of hybrid lesion segmentation based on both functional and structural information in accordance with the present disclosure.
Figure 5A:
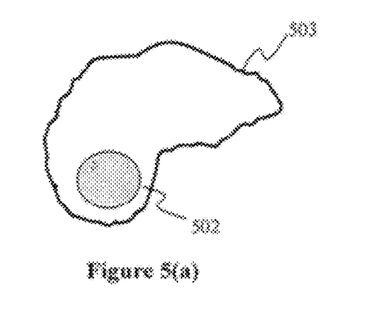
FIG. 5 depicts a construct of the combination of structural information in CT with functional information in SPECT for resection planning in accordance with the present disclosure.
Figure 5B:
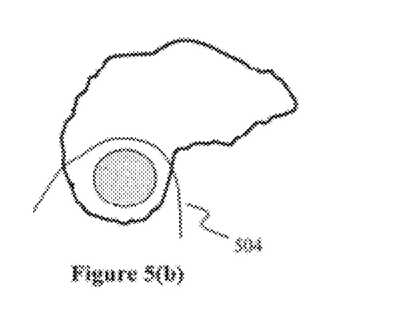
Figure 5C:
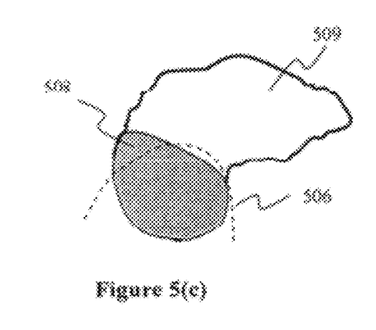
Figure 5D:
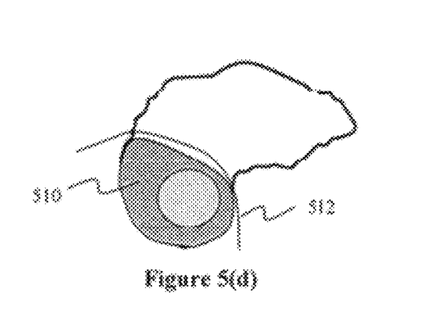

FIG. 4 depicts the steps and flow in an embodiment of hybrid lesion segmentation. At step 402, the intensity gradient of the SPECT image is computed for the functionally defect region. At step 404, the intensity gradient of the CT image is computed. At step 406, a hybrid gradient map is composed based on weighted sum of the SPECT gradient and CT gradient. The weights for the SPECT and CT gradient images may be computed as the inverse of the maximum gradient values for the SPECT and CT gradient images, respectively. This serves as a normalization of gradient values. At step 408, the CT image intensity is reorganized as a weighted valued of the original CT value and the functionally defect region. At step 410, a region is determined that maximizes the gradient at the region's boundary and at the same time minimize the variation for weighted CT intensity within the region.

FIG. 5 illustrates an embodiment of using SPECT for treatment planning based on functional analysis of liver in SPECT and anatomical analysis in CT. FIG. 5(a) shows a lesion 502 in the liver 503 in the CT image space. FIG. 5(b) shows a planned resection of the lesion in CT alone, in which the resection plane is indicated by 504. This would be the cutting plane when no SPECT images are available. FIG. 5(c) shows the functional map of the liver in SPECT, where label 509 indicates healthy liver tissue and label 508 indicates diseased liver tissue. The dashed curve 506 indicates the resection plane mapped from the CT space. It can be seen that resection plane does not completely cover the functionally defect area 508. This means that anatomical information based on the CT alone may not completely reflect the functional information of the liver. In FIG. 5(d), area 510 indicates the segmented lesion from hybrid segmentation. Based on the functional information in SPECT and the anatomical information in CT, a revised resection plane may be obtained, such as curve 512, which now includes all the functionally defective regions and the lesion.

Figure 6:
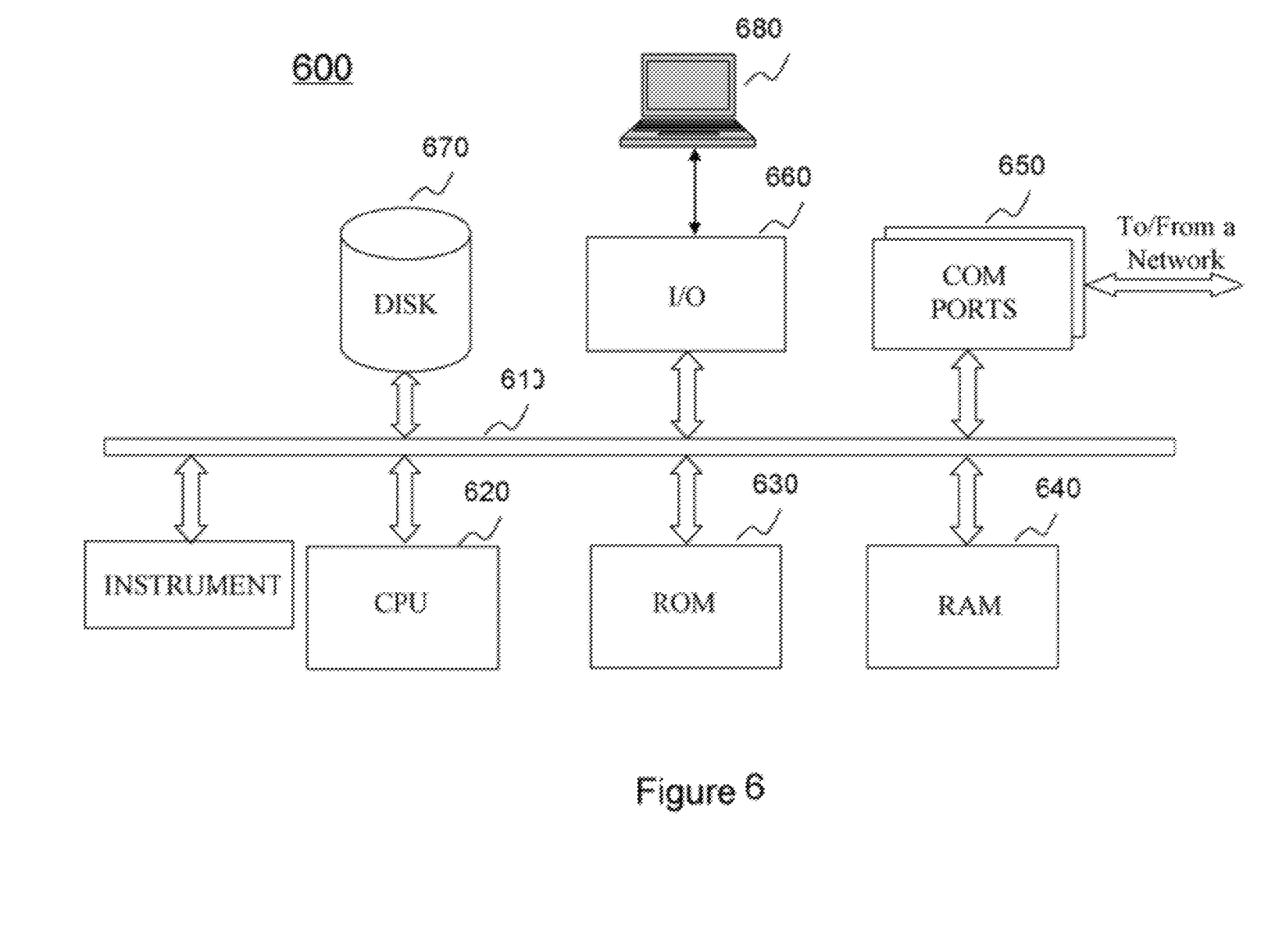
FIG. 6 depicts a computer system for carrying out the system and method of the present disclosure in accordance with the present disclosure.

FIG. 6 depicts a general computer architecture on which the present teaching can be implemented and has a functional block diagram illustration of a computer hardware platform which includes user interface elements. The computer may be a general purpose computer or a special purpose computer. This computer 600 can be used to implement any components of the treatment planning using SPECT-CT imaging as described herein. For example, the image display, image storing, image processing, can all be implemented on a computer such as computer 600, via its hardware, software program, firmware, or a combination thereof. Although only one such computer is shown, for convenience, the computer functions relating to the disclosure described herein may be implemented in a distributed fashion on a number of similar platforms, to distribute the processing load.

The computer 600, for example, includes COM ports 650 connected to and from a network connected thereto to facilitate data communications. The computer 600 also includes a central processing unit (CPU) 620, in the form of one or more processors, for executing program instructions. The exemplary computer platform includes an internal communication bus 610, program storage and data storage of different forms, e.g., disk 670, read only memory (ROM) 630, or random access memory (RAM) 640, for various data files to be processed and/or communicated by the computer, as well as possibly program instructions to be executed by the CPU. The computer 600 also includes an I/O component 660, supporting input/output flows between the computer and other components therein such as user interface elements 680. The computer 600 may also receive programming and data via network communications.

Hence, aspects of treatment planning in SPECT-CT imagery as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution. In addition, the treatment planning utilizing SPECT-CT imagery as disclosed herein can be implemented as a firmware, firmware/software combination, firmware/hardware combination, or a hardware/firmware/software combination. While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A method implemented on a machine having at least one processor comprising hardware, storage, and a communication platform connected to a network for generating a treatment plan for an organ disease, the method comprising:
    segmenting, by the at least one processor, an organ on a first image in a first imaging modality obtained from a first imaging device, the first imaging modality providing anatomical information of the organ;
    mapping, by the at least one processor, the segmented organ including a boundary of the organ from the first image onto a second image in a second imaging modality obtained from a second imaging device, the second imaging modality providing functional information of the organ;
    determining, by the at least one processor, a boundary of the organ on the second image based on the boundary of the organ mapped from the first image by geometrically transforming the boundary of the organ from the first image to the second image;
    identifying, by the at least one processor, one or more defective organ regions of the organ on the second image;
    segmenting, by the at least one processor, the one or more defective organ regions on the second image based on intensity of the second image and the boundary of the organ to the second image;
    mapping, by the at least one processor, the segmented one or more defective regions from the second image onto the first image;
    identifying, by the at least one processor, a target object on the first image based on a combination of intensity and intensity gradient of the one or more defective regions mapped from the second image and intensity and intensity gradient of the organ on the first image, wherein the identifying the target object is based on an optimization that maximizes a combined intensity gradient of the first image in the first imaging modality and the second image in the second imaging modality and minimizes an intensity variance within the target object;
    identifying, by the at least one processor, anatomical structures on the first image;
    combining, by the at least one processor, the segmented first image and the second image into a combined image;
    generating, by the at least one processor, one or more treatment plans based on the combined image, the target object, and the anatomical structures;
    determining, by the at least one processor, remnant organ function for each of the one or more treatment plans; and
    displaying the remnant organ function for each of the one or more treatment plans.

2. The method of claim 1, wherein the organ is a liver.

3. The method of claim 1, wherein the first imaging modality is a computerized axial tomography (CT) image.

4. The method of claim 1, wherein the second imaging modality is a single photon emission computed tomography (SPECT) image.

5. The method of claim 1, wherein the segmenting of the defective organ regions is based on a threshold measurement.

6. The method of claim 1, wherein the anatomical structures are vascular structures.

7. The method of claim 1, wherein the target object is a tumor.

8. The method of claim 1 further comprising:
    defining a safety margin that specifies a distance from a virtual cut to a surface of a hybrid segmented lesion.

9. The method of claim 8 wherein the safety margin is defined using a user adjustable interface.

10. The method of claim 1, wherein the combined image is a 3D virtual object that displays the one or more defective regions, the target object, and the segmented organ.

11. The method of claim 1, wherein the combined image is overlay of the one or more defective regions on the second image and the target object on the first image.

12. The method of claim 1, wherein identifying the target object on the first image comprises:
    computing a first inverse of maximum intensity gradient of the organ on the first image;
    computing a second inverse of maximum intensity gradient of the one or more defective regions mapped from the second image; and computing a weighted sum based on the first inverse of maximum intensity gradient and the second inverse of maximum intensity gradient.

13. The method of claim 1, wherein the target object covers the one or more defective regions mapped from the second image.

14. A machine-readable tangible and non-transitory medium, having information recorded thereon for generating a treatment plan of an organ disease, wherein the information, when read by the machine, causes the machine to perform the following:
  segmenting an organ on a first image in a first imaging modality obtained from a first imaging device, the first imaging modality providing anatomical information of the organ;
  mapping the segmented organ including a boundary of the organ from the first image onto a second image in a second imaging modality obtained from a second imaging device, the second imaging modality providing functional information of the organ;
  determining a boundary of the organ on the second image based on the boundary of the organ mapped from the first image by geometrically transforming the boundary of the organ from the first image to the second image;
  identifying one or more defective organ regions of the organ on the second image;
  segmenting the one or more defective organ regions on the second image based on intensity of the second image and the boundary of the organ geometrically transformed from the first image to the second image;
  mapping the segmented one or more defective regions from the second image onto the first image;
  identifying a target object on the first image based on a combination of intensity and intensity gradient of the one or more defective regions mapped from the second image and intensity and intensity gradient of the organ on the first image;
  wherein the identifying the target object is based on an optimization that maximizes a combined intensity gradient of the first image in the first imaging modality and the second image in the second imaging modality and minimizes an intensity variance within the target object;
  identifying anatomical structures on the first image;
  combining the segmented first image and the second image into a combined image;
  generating one or more treatment plans based on the combined image, the target object, and the anatomical structures;
  determining remnant organ function for each of the one or more treatment plans; and
  displaying the remnant organ function for each of the one or more treatment plans.

15. The medium of claim 14, wherein the organ is a liver.

16. The medium of claim 14, wherein the target object is a tumor.

17. The medium of claim 14, wherein the first imaging modality is a CT image.

18. The medium of claim 14 wherein the second imaging modality is a SPECT image.

19. The medium of claim 14, wherein the segmenting of the defective organ regions is based on a threshold measurement.

20. The medium of claim 14, wherein the anatomical structures are vascular structures.

21. The medium of claim 14 further comprising:
  defining a safety margin that specifies a distance from a virtual cut to a surface of a hybrid segmented lesion.

22. The medium of claim 21, wherein the safety margin is defined using a user adjustable interface.

* * * * *